(12) United States Patent
Bakala et al.

(10) Patent No.: US 8,697,652 B2
(45) Date of Patent: Apr. 15, 2014

(54) COSMETIC USE OF AT LEAST THE NATURAL TETRAPEPTIDE AC-SER-ASP-LYS-PRO OR ONE OF ITS ANALOGS AS A SKIN RESTRUCTURING AGENT

(75) Inventors: Joanna Bakala, Paris (FR); Jean-Yves Lallemand, Palaiseau (FR); Jian-Miao Liu, Ivry (FR); Jérôme Bignon, Le Val St Germain (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 1679 days.

(21) Appl. No.: 11/630,264

(22) PCT Filed: Jun. 22, 2005

(86) PCT No.: PCT/FR2005/001568
§ 371 (c)(1),
(2), (4) Date: Dec. 20, 2006

(87) PCT Pub. No.: WO2006/008392
PCT Pub. Date: Jan. 26, 2006

(65) Prior Publication Data
US 2007/0259819 A1    Nov. 8, 2007

(30) Foreign Application Priority Data
Jun. 23, 2004 (FR) ................................. 04 06822

(51) Int. Cl.
| *A61K 8/64* | (2006.01) |
|---|---|
| *A61K 8/00* | (2006.01) |
| *A61P 17/00* | (2006.01) |
| *A61K 38/07* | (2006.01) |
| *A61K 38/00* | (2006.01) |
| *A61K 9/00* | (2006.01) |
| *A61Q 19/00* | (2006.01) |
| *A61Q 19/08* | (2006.01) |

(52) U.S. Cl.
CPC ................. *A61K 38/07* (2013.01); *A61K 38/00* (2013.01); *A61K 8/64* (2013.01); *A61K 9/0014* (2013.01); *A61Q 19/00* (2013.01); *A61Q 19/08* (2013.01)

USPC ...... 514/18.6; 514/18.8; 514/21.9; 424/78.03

(58) Field of Classification Search
None
See application file for complete search history.

(56) References Cited

U.S. PATENT DOCUMENTS 5,348,943 A * 9/1994 Pickart ............................ 514/18
5,492,894 A    2/1996 Bascom et al.

FOREIGN PATENT DOCUMENTS

| JP | 2-178207 A | 7/1990 |
|---|---|---|
| WO | WO 88/00594 A1 | 1/1988 |
| WO | WO 97/28183 A1 | 8/1997 |
| WO | WO 02/24218 A1 | 3/2002 |
| WO | WO-0224218 A1 * | 3/2002 ............. A61K 38/00 |

OTHER PUBLICATIONS

Bakala et al. (2002) Machine translation of WO-0224218-A1. Retrieved Oct. 27, 2009 via Google Translate.*
Sadick et al. (2009). Cosmetic dermatology of the aging face. Clinics in Dermatology, vol. 27, Issue 3, Supplement 1, pp. S3-S12.*

* cited by examiner

*Primary Examiner* — Kevin S Orwig
(74) *Attorney, Agent, or Firm* — Foley & Lardner LLP

(57) ABSTRACT

This invention relates to the cosmetic use of at least one compound of formula (I)

$$R_1 \diagdown N - \underset{\underset{H}{|}}{\overset{\overset{A_1}{|}}{C}} - X_1 - \underset{\underset{H}{|}}{\overset{\overset{A_2}{|}}{C}} - X_2 - \underset{\underset{H}{|}}{\overset{\overset{A_3}{|}}{C}} - X_3 - A_4 - R_3 \quad (I)$$
$$R_2 \diagup$$

wherein
$A_1$ is the radical corresponding to D- or L-Ser
$A_2$ is the radical corresponding to D- or L-Asp or Glu,
$A_3$ is the radical corresponding to D- or L-Lys, Arg or Orn,
$A_4$ is the radical corresponding to D- or L-pro,
$R_1$, $R_2$ and $R_3$ are as defined in the claims as anti-aging and restructuring agents.

10 Claims, 5 Drawing Sheets

control
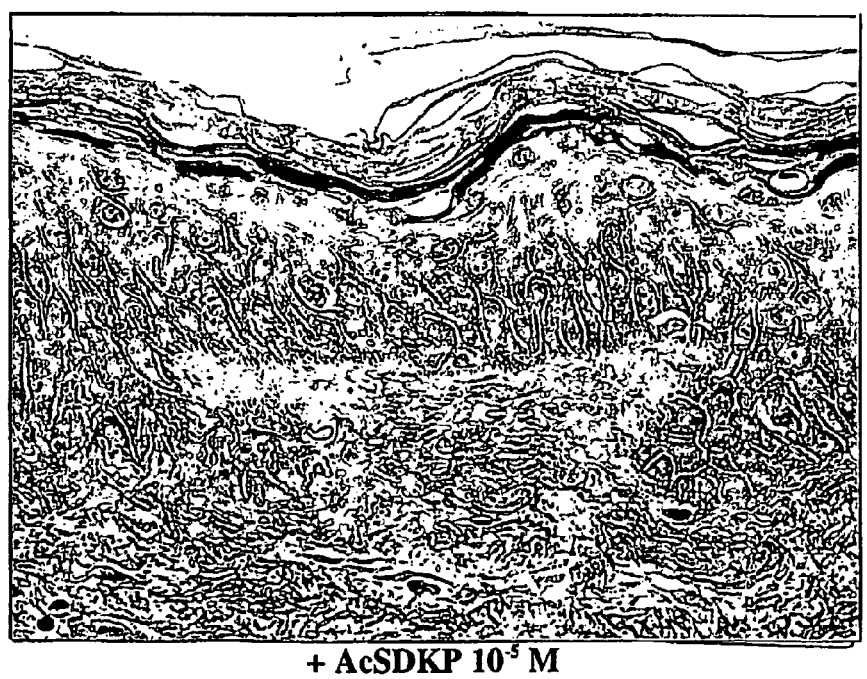
+ AcSDKP $10^{-5}$ M
Fig. 1. General morphology (Masson Trichrome staining) of human skins explants at 6th survival day.

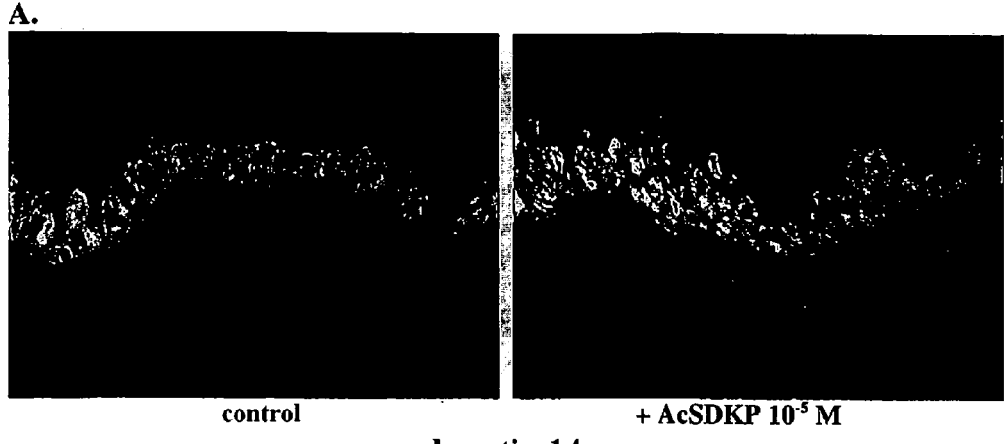
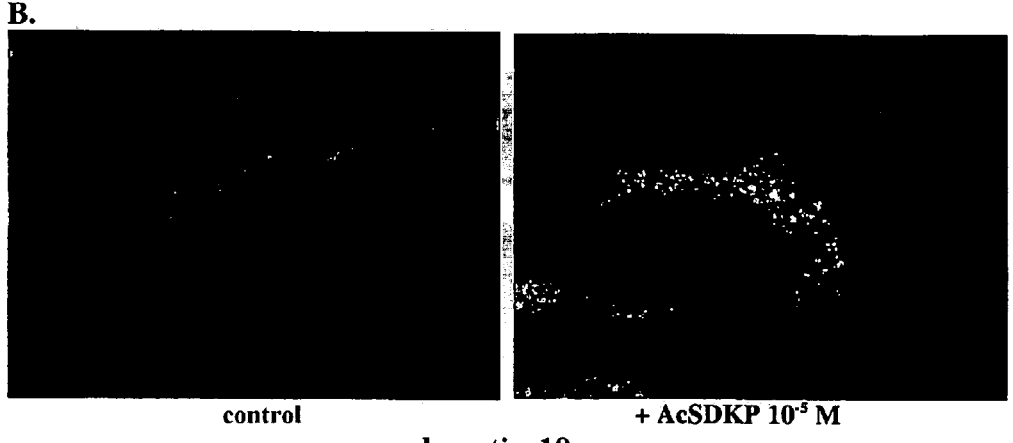
Fig. 2. Keratin 14 and 19 expression in the human skins explants at 6th survival day.

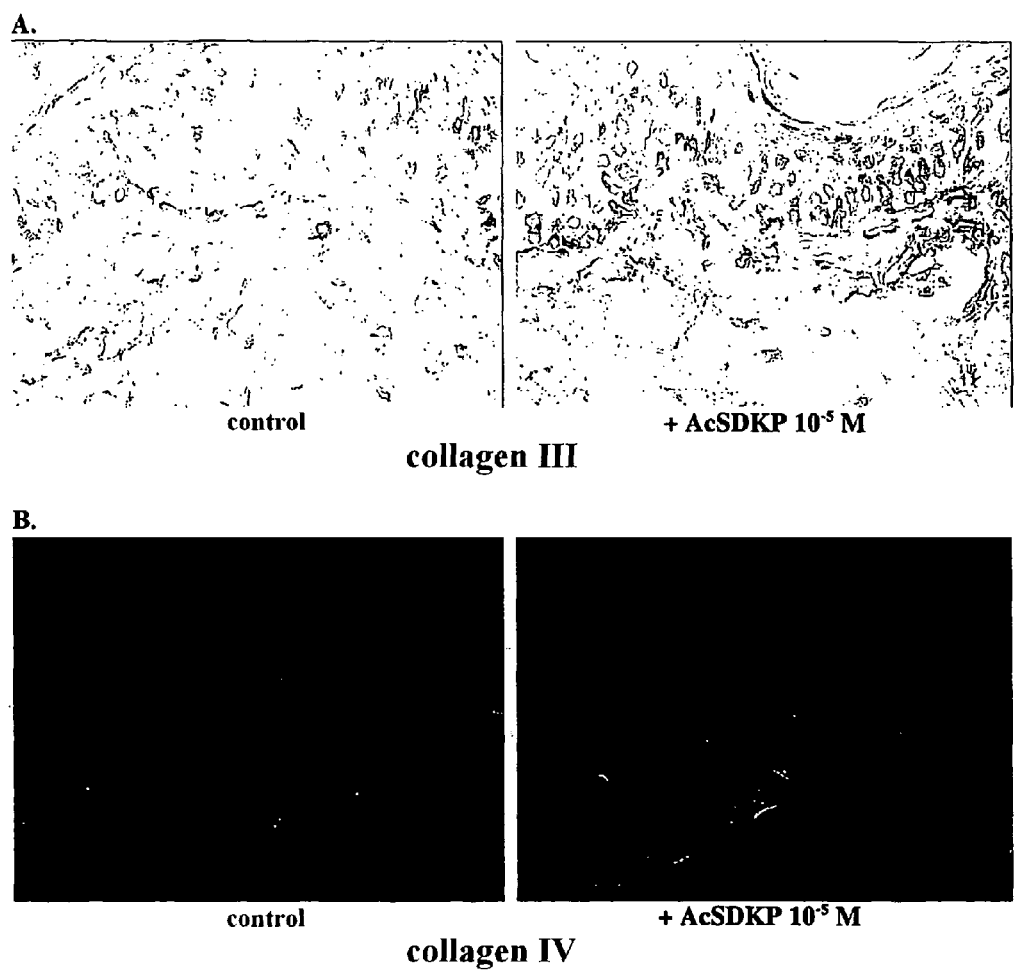
Fig. 3. Collagen III and collagen IV expression in the human skins explants at 6th survival day

control
AcSDKP $10^{-5}$ M
Fig. 4. Fibronectin expression in human skins explants at 6th survival day.

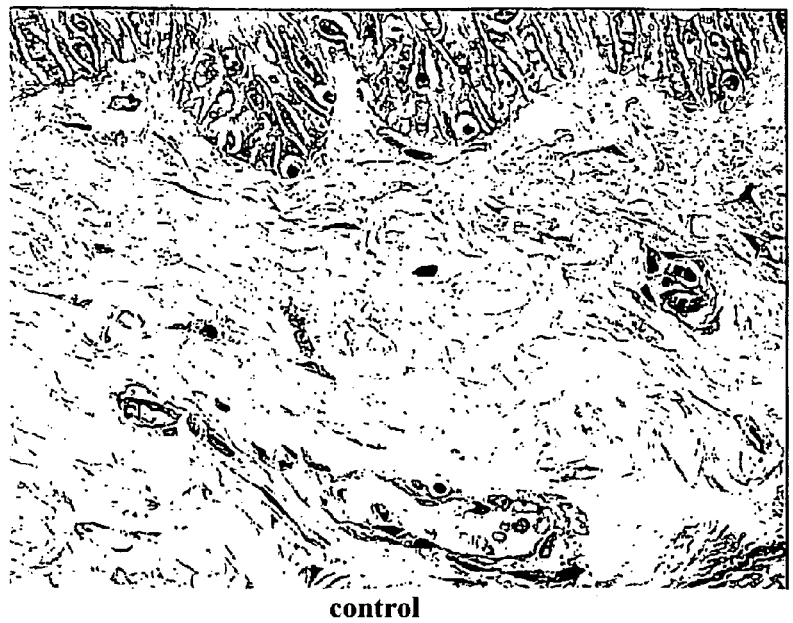
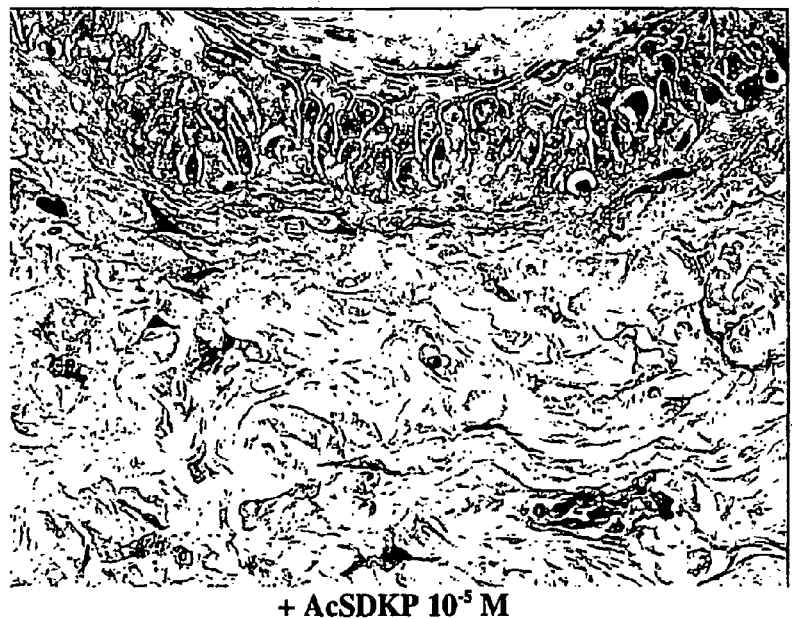
Fig. 5. Glycosaminoglycan expression in human skins explants at 6th survival day.

COSMETIC USE OF AT LEAST THE NATURAL TETRAPEPTIDE AC-SER-ASP-LYS-PRO OR ONE OF ITS ANALOGS AS A SKIN RESTRUCTURING AGENT

This application is a National Stage application of PCT/FR2005/001568, filed Jun. 22, 2005, which claims priority from French patent application FR 0406822, filed Jun. 23, 2004. The entire contents of each of the aforementioned applications are incorporated herein by reference.

This invention relates to the cosmetic use in a composition of at least one tetrapeptide or analogue as a skin anti-aging and restructuring agent.

Skin consists of a set of cells grouped together in the form of supple, resistant tissue covering the whole of the body. The main role played by skin is as a protective barrier against external factors at the same time as allowing certain exchanges between the interior and exterior environment. It is the site of many metabolic processes that are regulated by the organism's physiological conditions and environmental conditions. Skin consists of two adjacent layers, the epidermis and the dermis, to which subcutaneous tissue is attached.

The epidermis, whose principal role is to protect the body, is the uppermost layer of the skin and gives the skin its impermeability and resistance. It is renewed approximately every four weeks. While different cell types co-exist in the epidermis, the keratinocytes constitute the main cell type (90%). Their characteristic activity is that of keratin synthesis which make up 95% of the epidermis' total proteins. The keratins, fibrous and water-insoluble proteins, are constituents of the corneal layer of the epidermis which protects the skin against harmful external factors (heat, cold, dehydration).

The epidermis is connected to the dermis through a zone called the dermo-epidermal junction or epidermal basal membrane. This structure provides adhesion of the dermis to the epidermis and has a mechanical support role which is partly responsible for skin tonicity. It is made up of both basal keratinocytes and dermal fibroblasts and contains a high level of type IV collagen which partly makes up the anchorage plates linking the basal membrane to the anchorage plates in the papillary dermis.

The dermis, the skin's inner layer, is a fibro-elastic conjunctive tissue comprised of cells (fibroblasts) dispersed in a complex medium called the extracellular matrix. This matrix consists of collagen and elastin fibres, glycoproteins (fibronectin and laminin) and proteoglycans (central protein+ glycosaminoglycans of GAGs). The nature and quantity of these constituents regulate the skin's mechanical properties and are responsible for the most noticeable physiopathological changes noted in the course of aging. The fibres give the skin solidity, resistance, elasticity and tonicity while the glycoproteins and proteoglycans provide volume and contribute to hydration.

The collagens, proteins which make up 75% of the dermis, represent the dermis' "cement". Their particular spatial arrangement confers rigidity on the collagen molecule and thus contributes its to the mechanical function. Type III fibrillar collagen whose dermal site is known, constitutes an essential component of the fibrous network and plays a mechanical role in ensuring a large proportion of the skin's support and elasticity.

The proteoglycans, large complex macromolecules scattered between the fibres of dermal conjunctive tissue, are responsible for a large part of the skin's tonicity. The structure of the glycosaminoglycans (GAGs), polymers consisting of long polysaccharide chains, which confer negative charges on the proteoglycans allowing them to "capture" ions, water and various metabolites, thus contribute to skin moisture and resistance to pressure and stretch forces.

In the course of aging, skin becomes wrinkled, looser, less hydrated and is renewed less easily. The clinical symptoms that affect appearance or cause skin diseases are essentially due to the effect of UV and harmful external factors, such as pollution, as well as to so-called "intrinsic" factors corresponding to chronological aging which begins at the age of 20 years.

The epidermis is the first to be affected by aging. The ability of the keratinocytes to divide in the basal layer decreases and the renewal time for the upper corneal layer becomes longer. Cell maturation is imperfect and keratinisation no longer results in the formation of a regular, homogeneous basal layer. This leads to the epidermis becoming less thick, more dry and rougher in appearance.

At the same time, there is disorganisation of the deeper areas of the skin. The dermis, responsible for both basic cohesion and nutrition functions, is the main target of cutaneous damage. In the course of aging, the fibroblasts, the source of the dermis' constituent substances, disappear or are changed into fibrocytes. Consequently, the levels of fibronectin, which plays an important role in cell adhesion and function, are diminished. There is also a reduction in the number and quality of elastic fibres. The reduced amount of collagen (1% per year) explains the loss of dermal elasticity and reduced skin thickness. Loss of suppleness in the connections binding the dermal cells to each other is the root cause of the signs of wear and tear seen in elderly people. This also explains the appearance of bags under the eyes and cutaneous wrinkles, as well as the accentuation of dermal lesions following minimal trauma.

Longer life expectancy combined with the desire to retain a youthful appearance have motivated research into skin structure changes that occur in the course of the aging process. The main components responsible for our appearance are the skin's structural tissues (conjunctive, corneal and fibroplasmic). Among their constituent substances, the collagens, elastins and keratins play a vital role in the morphological alterations that affect skin. It is partly at this level that cosmetic products work. There are a multitude of facial lift programmes and treatments available on the market to reduce wrinkles and improve skin elasticity. The majority of these work on the skin's surface or only on the target proteins mentioned above and their effects are temporary and partially satisfactory.

Moreover, many compounds are not totally devoid of toxicity and long-term application can lead to skin problems such as allergies. The processes used for their manufacture often involve chemical synthesis or long and costly extraction processes from natural substances.

This is why there is always a need for compounds that do not present these disadvantages (i.e. they are non-toxic and easy to obtain) and which act simultaneously on several protein targets.

Surprisingly, the Applicant has discovered that certain natural tetrapeptides or their analogues act on several levels simultaneously, both in the dermis and epidermis. These derivatives also have the advantage of being easy to isolate from the natural peptide or, alternatively, they can be obtained through peptide synthesis pathways that are easy to set up and, consequently, less expensive. In addition, and as a result of their peptidic nature, these compounds are not at all or only very slightly toxic to the organism.

The peptides or analogues used within the scope of this invention are derivatives of the basic structure Acetyl-Ser-Asp-Lys-Pro (AcSDKP). They are known for their therapeutic properties, particularly for bone marrow protection during anti-cancer treatment with chemotherapy, and for their capacity to inhibit the proliferation of haematopoietic cells (WO-88/00594 and WO-97/28183). Finally, the Applicant has more recently discovered their angiogenic properties (WO-02/24218).

There are no documents of the prior art that describe or suggest that these compounds might have an anti-aging or restructuring effect on the skin nor that their use leads to a positive effect on the synthesis of collagen III and IV, fibronectin, glycosaminoglycan and/or keratin.

BRIEF DESCRIPTION OF THE DRAWINGS

FIG. 1 shows general morphology (Masson Trichrome) staining of human skins explants at $6^{th}$ survival day.

FIG. 2 shows keratin 14 and 19 expression in the human skins explants at $6^{th}$ survival day.

FIG. 3 shows collagen III and collagen IV expression in the human skins explants at $6^{th}$ survival day.

FIG. 4 shows fibronectin expression in human skins explants at $6^{th}$ survival day.

FIG. 5 shows glycosaminoglycan expression in human skins explants at $6^{th}$ survival day.

This invention therefore relates to the cosmetic use of at least one compound of formulae (I):

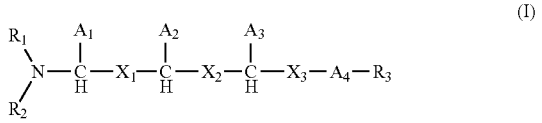

wherein
- $A_1$ is the radical corresponding to D- or L-Ser
- $A_2$ is the radical corresponding to D- or L-Asp or Glu,
- $A_3$ is the radical corresponding to D- or L-Lys, Arg or Orn,
- $A_4$ is the radical corresponding to D- or L-pro,
- $R_1$ and $R_2$ are independently chosen from among the hydrogen atom, a substituted or nonsubstituted $C_1$-$C_{12}$ linear or branched alkyl group, a substituted or nonsubstituted $C_7$-$C_{20}$ linear or branched arylalkyl group, $R_4CO$— and $R_4COO$— wherein $R_4$ is a substituted or nonsubstituted $C_1$-$C_{12}$ linear or branched alkyl group, or a substituted or nonsubstituted $C_7$-$C_{20}$ arylalkyl group. Substitutions include OH, $NH_2$ or COOH,
- $X_1$ and $X_2$ are peptide and pseudopeptide bonds,
- $X_3$ is a radical chosen among —CO— and —$CH_2$— and
- $R_3$ is a group chosen from among —OH, —$NH_2$, $C_1$-$C_{12}$ linear or branched alcoxy or —NH—$X_4$—$CH_2$—Z wherein $X_4$ is a $C_1$-$C_{12}$ linear or branched hydrocarbon group and Z is a hydrogen atom or —OH, —$CO_2H$ or —$CONH_2$ group, as well as their physiologically acceptable salts, in a composition as skin restructuring and anti-aging agents The preferred alkyl groups particularly suited to application of this invention are the $C_1$-$C_6$ linear or branched alkyl groups. More particularly, methyl, ethyl, propyl, isopropyl, butyl, isobutyl or tertbutyl groups are preferred.

The aryl group according to this invention refers to an aromatic carbon group with six to fourteen carbon atoms. An example of this is the phenyl, naphthyl or anthracenyl group.

The preferred arylalkyl groups according to the invention include the benzyl and phenethyl groups.

The peptides or pseudopeptide corresponding to formula (I) are derived from the tetrapeptide base structure Acetyl-Ser-Asp-Lys-Pro (AcSDKP)

The term "radical corresponding to" refers to radical A of formula:

$NH_2$—CH(A)-COOH corresponding to the amino acid.

A is therefore
- —$CH_2OH$ for Ser,
- —$CH_2COOH$ for Asp,
- —$CH_2$—$CH_2$—COOH for Glu
- —$(CH_2)_3$—NH—C(NH)$NH_2$ for Arg,
- —$(CH_2)_3$—$NH_2$ for Orn and
- —$(CH_2)_4$—$NH_2$ for Lys, for the terminal amino acid $A_4$, this refers to either =N—CH(A)-CO— or NH—(CH)A-CO—

The term "pseudopeptide" refers to compounds that are similar to the reference peptide but in which one or more peptide bonds —CO—NH— are substituted by a bond that is equivalent to the peptide bond, called a pseudopeptide, such as —$CH_2$—NH—, —$CH_2$—S—, —$CH_2$—O—, —CO—$CH_2$—CO—, —$CH_2$—$CH_2$— represented by Ψ ($CH_2NH$) for example.

Among the $R_1$ and $R_2$ radicals, the hydrogen atom or $R_4CO$— radicals wherein $R_4$ represents a $C_1$-$C_3$ alkyl group, notably $CH_3CO$ as well as HOOC—$CH_2$—$CH_2$—CO—O, are preferred.

Similarly, $R_3$ is preferably $NH_2$, OH or $NHCH_3$.

The compounds of formula (I) suited to implementation of the invention include:

$CH_3CO$-Ser-Asp-Lys-Pro-OH
$CH_3CO$-Ser-Ψ-($CH_2NH$)-Asp-Lys-Pro-OH
$CH_3CO$-Ser-Asp-Ψ-($CH_2NH$)-Lys-Pro-OH
$CH_3CO$-Ser-Asp-Lys-Ψ-($CH_2N$)—Pro-OH
$CH_3CO$-Ser-Ψ-($CH_2NH$)-Asp-Lys-Pro-$NH_2$
$CH_3CO$-Ser-Asp-Ψ-($CH_2NH$)-Lys-Pro-$NH_2$
$CH_3CO$-Ser-Asp-Lys-Ψ-($CH_2N$)-Pro-$NH_2$
H-Ser-Ψ-($CH_2NH$)-Asp-Lys-Pro-OH
H-Ser-Asp-Ψ-($CH_2NH$)-Lys-Pro-OH
H-Ser-Asp-Lys-Ψ-($CH_2N$)-Pro-OH
HOOC$CH_2CH_2$CO-Ser-Ψ-($CH_2NH$)-Asp-Lys-Pro-OH
HOOC$CH_2CH_2$CO-Ser-Asp-Ψ-($CH_2NH$)-Lys-Pro-OH
HOOC$CH_2CH_2$CO-Ser-Asp-Lys-Ψ-($CH_2N$)-Pro-OH
H-Ser-Ψ-($CH_2NH$)-Asp-Lys-Pro-$NH_2$
H-Ser-Asp-Ψ-($CH_2NH$)-Lys-Pro-$NH_2$
H-Ser-Asp-Lys-Ψ-($CH_2N$)-Pro-$NH_2$
HOOC$CH_2CH_2$CO-Ser-Ψ-($CH_2NH$)-Asp-Lys-Pro-$NH_2$
HOOC$CH_2CH_2$CO-Ser-Asp-Ψ-($CH_2NH$)-Lys-Pro-$NH_2$
HOOC$CH_2CH_2$CO-Ser-Asp-Lys-Ψ-($CH_2N$)-Pro-$NH_2$
$CH_3CO$-Ser-Asp-Lys-Pro-$NH_2$
H-Ser-Asp-Lys-Pro-$NH_2$
$CH_3CO$-Ser-Asp-Lys-Pro-$NHCH_3$
H-Ser-Asp-Lys-Pro-$NHCH_3$
HOOC$CH_2CH_2$CO-Ser-Asp-Lys-Pro-$NHCH_3$
HOOC$CH_2CH_2$CO-Ser-Asp-Lys-Pro-$NH_2$

One compound of formula (I) particularly suited to implementation of this invention is the natural tetrapeptide $CH_3CO$-Ser-Asp-Lys-Pro (AcSDKP)

The term "physiologically acceptable salt" according to this invention refers to any salt prepared from any physiologically acceptable non-toxic acid, including organic and inorganic acids. Such acids include acetic, benzenesulfonic, benzoic, citric, ethanesulfonic, fumaric, gluconic, glutamic, hydrobromic, hydrochloric, lactic, maleic, malic, mandelic, methanesulfonic, mucic, nitric, pamoic, pantothenic, phosphoric, succinic, tartaric and paratoluenesulfonic acids. Advantageously, hydrochloric acid is used.

One embodiment of this invention relates to the cosmetic use of a composition of formula (I) as defined above in a composition as a stimulating agent for the production of collagen III and IV, fibronectin, glycosaminoglycans and/or keratin 14 and/or 19.

More particularly, this invention relates to the use of a compound of formula (I) as defined above in a composition as an agent to prevent intrinsic skin aging.

Advantageously, the compounds of formula (I) as defined above can be used to improve skin elasticity and/or tonicity, and/or to prevent, reduce, and/or suppress the appearance of wrinkles and crow's-feet on the skin.

According to another aspect of the invention, compounds of formula (I) as defined above can be used to improve skin regeneration after dermabrasion, chemical peeling or laser resurfacing treatment.

The natural tetrapeptide $CH_3CO$-Ser-Asp-Lys-Pro (AcSDKP) has been isolated from calf foetus bone marrow (WO-88/00594). It can also be obtained by conventional peptide synthesis. The peptides or pseudopeptides of formula (I) derived from AcSDKP can also be obtained by means of peptide or pseudopeptide synthesis, as described in the document WO-97/28183.

The compounds of formula (I) are present in the compositions used to implement this invention in amounts ranging from 0.01% and 10% by weight, preferably between 0.05% and 5% by weight, and more particularly between 0.1% and 2% by weight with respect to the total weight of the composition.

The cosmetic compositions according to the invention are for topical use and can be used in any pharmaceutical form conventionally used for this type of application, notably in the form of emulsions (oil-in-water, water-in-oil, triple oil-in-water-in-oil or water-in-oil-in-water emulsion), aqueous gels or aqueous, hydroalcohol or oily solutions. They are more or less fluid and in the form of a white or coloured cream, ointment, milk, lotion, serum, paste, moose, or in a biphasic form. There can also be in a solid form, for example in stick or aerosol form.

The composition used within the scope of this invention contains, in addition to derivatives of formula (I), one or more excipients which can be chosen from among compounds with good compatibility with the active ingredients present in the formula. For example, this can be hydrosoluble polymers derived from natural polymers such as the polysaccharides (xanthane gum, carob gum, peptin) or polypeptides, cellulose derivatives such as methylcellulose, hydroxypropylcellulose, hydroxypropyl-methylcellulose or synthetic polymers, polaxamers, carbomers, PVA and PVP.

Finally the composition can also contain various other excipients of the cosolvent type such as ethanol, glycerol, benzyl alcohol, wetting agent (glycerol), agents which facilitate diffusion (transcurol, urea) or antibacterial agents (0.15% methyl p-hydroxybenzoate). They can also contain surfactants, stabilising agents, emulsifiers, thickening agents and other active ingredients which have a complementary or synergetic effect, as well as trace elements, essential oils, fragrances, dyes, collagen, chemical or mineral filters, moisturizing agents or spa waters.

In a particular embodiment of the invention, the derivatives of formula (I) are combined with at least one other active ingredient.

This invention also relates to a cosmetic process for the treatment of skin aging involving application to the skin of a composition containing at least one derivative of formula (I) as defined above.

The examples below illustrate the invention but are in no way limiting.

EXAMPLE 1

Study of the Restructuring and Anti-Aging Activity of a Preparation Containing the Tetrapeptide AcSDKP This study was conducted on thirty six human skin explants obtained from breast plastic surgery.

Method

All the explants were maintained in a state of survival in a culture medium for eight days. AcSDKP at a concentration of $10^{-5}$ M or $10^{-8}$ M in physiological serum was applied to the explants by topical route every day for one week. On days 2, 4, 6 and 8, three explants from each batch (control, +AcSDKP $10^{-5}$ M+ AcSDKP $10^{-8}$ M) were removed and prepared for histological studies. General morphology was examined and an evaluation of the expression of basal keratin (CK14), undifferentiated keratin (CK19), collagen III, collagen IV, fibronectin and glycosaminoglycan without an acid group was performed.

Results

1. General Morphology

Examination of the set of explants shows that application of AcSDKP at the two concentrations tested triggers stimulation of the epidermal structure as of D6 of treatment. This is seen by an increased number of live cell bases. The increase in epidermal thickness is greater following application of AcSDKP $10^{-5}$ M (FIG. 1)

2. Keratin 14 (CK14) and Keratin 19 (CK19) Expression

Immunolabelling of CK14 revealed a gradual increase in the levels of this protein in the basal and superbasal position as of D4 of treatment. The restructuring effect is greater with AcSDKP $10^{-5}$ M (FIG. 2A). Immunolabelling of CK19 made it possible to observe overexpression of the skin's dermal attachments as of D6 of treatment with AcSDKP at the two concentrations tested. AcSDKP at a concentration of $10^{-5}$ M has a less marked effect (FIG. 2B).

AcSDKP therefore stimulates the production of CK14 and CK19 in treated skin.

3. Dermal Collagen (Type III) and Basal Membrane Collagen (Type IV) Expression

There is a very marked increase in collagen III levels in the papillary dermis along the dermo-epidermal junction after six days of treatment with AcSDKP $10^{-5}$ M (FIG. 3A). This expression along the dermo-epidermal junction is less pronounced with AcSDKP $10^{-8}$ M. However, collagen III is more present in the remainder of the papillary dermis and reticular dermis. On D8, there is very clear overexpression of collagen III in the papillary and reticular dermis of explants treated with AcSDKP $10^{-5}$ M. With AcSDKP $10^{-8}$ M, the level of collagen III increases along the dermo-epidermal junction and forms a thicker collagen band.

The increase in collagen IV levels in the basal membrane along the dermo-epidermal junction at D6 and D8 is less pronounced than that for type III collagen in skin treated with AcSDKP at the two concentrations tested and is higher for AcSDKP $10^{-5}$ M (FIG. 3B).

Immunolabelling of collagen III and IV revealed that AcSDKP has stimulatory effect on the expression of these compounds in treated skin.

4. Fibronectin Expression

The fibronectin network is denser and has thicker fibres in the area treated with AcSDKP. There is greater activity for AcSDKP tested at a concentration of $10^{-5}$ M (FIG. 4).

Immunolabelling of fibronectin shows that AcSDKP triggers overexpression of this protein along a dermo-epidermal junction as well as in the papillary and reticular dermis of treated skin.

5. Glycosaminoglycan (GAGs)

Histological cuts of skins explants stained with P.A.S. Alcian blue specific to GAGs without acid groups revealed a significant increase in the levels of these compounds in the skin following treatment of explants with AcSDKP at the two concentrations tested. This effect, clearly visible at D6 and D8, is characterised by a PAS positive increase in the number of fibroblasts in the papillary dermis, especially in the band situated along the dermo-epidermal junction and by increased levels of GAGs in these fibroblasts. AcSDKP applied at a concentration of $10^{-5}$ M shows a higher level of activity than when the tetrapeptide is used at a concentration of $10^{-8}$ M (FIG. 5).

Conclusion

The observations described above show a restructuring of the epidermis and dermis under the effect of the tetrapeptide AcSDKP. These modifications are representative of the criteria for younger skin.

The following formulae are prepared in accordance with the conventional methods used by the man skilled in the art.

EXAMPLE 2

Oil-In-Water Emulsion

| | |
|---|---|
| Polyethylene glycol oxyethylene per 50 moles ethylene oxide | 3% |
| Monodiglycerylstearate | 3% |
| Vaseline oil | 3% |
| Ketyl alcohol | 5% |
| AcSDKP | 2% |
| Water | qs 100% |

EXAMPLE 3

| | |
|---|---|
| Octylpalmitate | 10% |
| Glycerylisostearate | 4% |
| Vaseline oil | 10% |
| Sorbitol | 2% |
| Vitamin E | 1% |
| AcSDKP | 0.5% |
| Glycerol | 3% |
| Water | qs 100% |

The invention claimed is:

1. A method for reducing and/or suppressing wrinkles or crow's-feet on skin comprising applying to the skin of a patient in need thereof of an effective amount of a composition containing at least one compound of formula (I):

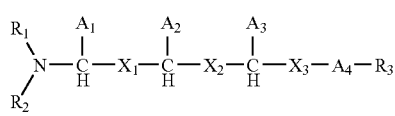

wherein
$A_1$ is the radical corresponding to D- or L-Ser
$A_2$ is the radical corresponding to D- or L-Asp or Glu,
$A_3$ is the radical corresponding to D- or L-Lys, Arg or Orn,
$A_4$ is the radical corresponding to D- or L-pro,
$R_1$ and $R_2$ are independently chosen from among the hydrogen atom, a substituted or nonsubstituted $C_1$-$C_{12}$ linear or branched alkyl group, a substituted or nonsubstituted $C_7$-$C_{20}$ linear or branched arylalkyl group, $R_4$CO— and $R_4$COO— wherein $R_4$ is a substituted or nonsubstituted $C_1$-$C_{12}$ linear or branched alkyl group, or a substituted or nonsubstituted $C_7$-$C_{20}$ arylalkyl group, substitutions include OH, $NH_2$ or COOH,
$X_1$ and $X_2$ are peptide and pseudopeptide bonds,
$X_3$ is a radical chosen among —CO— and —$CH_2$—, and
$R_3$ is a group chosen from among —OH, —$NH_2$, $C_1$-$C_{12}$ linear or branched alkoxy or —NH—$X_4$—$CH_2$—Z wherein $X_4$ is a $C_1$-$C_{12}$ linear or branched hydrocarbon group and Z is a hydrogen atom or —OH, —$CO_2$H or —$CONH_2$ group, as well as their physiologically acceptable salts.

2. The method according to claim 1, wherein the compound of formula (I) includes at least one pseudopeptide bond.

3. The method according to claim 1, wherein the compound of formula (I) is chosen from among:

$CH_3$CO-Ser-Asp-Lys-Pro-OH
$CH_3$CO-Ser-Ψ-($CH_2$NH)-Asp-Lys-Pro-OH
$CH_3$CO-Ser-Asp-Ψ-($CH_2$NH)-Lys-Pro-OH
$CH_3$CO-Ser-Asp-Lys-Ψ-($CH_2$N)-Pro-OH
$CH_3$CO-Ser-Ψ-($CH_2$NH)-Asp-Lys-Pro-$NH_2$
$CH_3$CO-Ser-Asp-Ψ-($CH_2$NH)-Lys-Pro-$NH_2$
$CH_3$CO-Ser-Asp-Lys-Ψ-($CH_2$N)-Pro-$NH_2$
H-Ser-Ψ-($CH_2$NH)-Asp-Lys-Pro-OH
H-Ser-Asp-Ψ-($CH_2$NH)-Lys-Pro-OH
H-Ser-Asp-Lys-Ψ-($CH_2$N)-Pro-OH
HOOC$CH_2$$CH_2$CO-Ser-Ψ-($CH_2$NH)-Asp-Lys-Pro-OH
HOOC$CH_2$$CH_2$CO-Ser-Asp-Ψ-($CH_2$NH)-Lys-Pro-OH
HOOC$CH_2$$CH_2$CO-Ser-Asp-Lys-Ψ-($CH_2$N)-Pro-OH
H-Ser-Ψ-($CH_2$NH)-Asp-Lys-Pro-$NH_2$
H-Ser-Asp-Ψ-($CH_2$NH)-Lys-Pro-$NH_2$
H-Ser-Asp-Lys-Ψ-($CH_2$N)-Pro-$NH_2$
HOOC$CH_2$$CH_2$CO-Ser-Ψ-($CH_2$NH)-Asp-Lys-Pro-$NH_2$
HOOC$CH_2$$CH_2$CO-Ser-Asp-Ψ-($CH_2$NH)-Lys-Pro-$NH_2$
HOOC$CH_2$$CH_2$CO-Ser-Asp-Lys-Ψ-($CH_2$N)-Pro-$NH_2$
$CH_3$CO-Ser-Asp-Lys-Pro-$NH_2$
H-Ser-Asp-Lys-Pro-$NH_2$
$CH_3$CO-Ser-Asp-Lys-Pro-NH$CH_3$
H-Ser-Asp-Lys-Pro-NH$CH_3$
HOOC$CH_2$$CH_2$CO-Ser-Asp-Lys-Pro-NH$CH_3$
HOOC$CH_2$$CH_2$CO-Ser-Asp-Lys-Pro-$NH_2$.

4. The method according to claim 1, wherein the compound of formula (I) is represented by the formula: $CH_3$CO-Ser-Asp-Lys-Pro-OH.

5. The method according to claim 1, wherein the compound of formula (I) is present in the composition in an amount ranging from 0.01% to 10% by weight with respect to the total weight of the composition.

6. A method for improving regeneration of skin after dermabrasion, chemical peeling, or laser resurfacing treatment comprising applying to the skin of a patient in need thereof after dermabrasion, chemical peeling, or laser resurfacing treatment an effective amount of a composition containing at least one compound of formula (I):

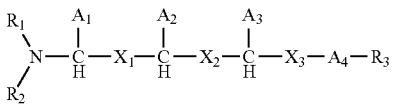 (I)

wherein
- $A_1$ is the radical corresponding to D- or L-Ser
- $A_2$ is the radical corresponding to D- or L-Asp or Glu,
- $A_3$ is the radical corresponding to D- or L-Lys, Arg or Orn,
- $A_4$ is the radical corresponding to D- or L-pro,
- $R_1$ and $R_2$ are independently chosen from among the hydrogen atom, a substituted or nonsubstituted $C_1$-$C_{12}$ linear or branched alkyl group, a substituted or nonsubstituted $C_7$-$C_{20}$ linear or branched arylalkyl group, $R_4CO$— and $R_4COO$— wherein $R_4$ is a substituted or nonsubstituted $C_1$-$C_{12}$ linear or branched alkyl group, or a substituted or nonsubstituted $C_7$-$C_{20}$ arylalkyl group, substitutions include OH, $NH_2$ or COOH,
- $X_1$ and $X_2$ are peptide and pseudopeptide bonds,
- $X_3$ is a radical chosen among —CO— and —$CH_2$—, and
- $R_3$ is a group chosen from among —OH, —$NH_2$, $C_1$-$C_{12}$ linear or branched alkoxy or —NH—$X_4$—$CH_2$—Z wherein $X_4$ is a $C_1$-$C_{12}$ linear or branched hydrocarbon group and Z is a hydrogen atom or —OH, —$CO_2H$ or —$CONH_2$ group, as well as their physiologically acceptable salts.

7. The method according to claim 6, wherein the compound of formula (I) includes at least one pseudopeptide bond.

8. The method according to claim 6, wherein the compound of formula (I) is chosen from among:

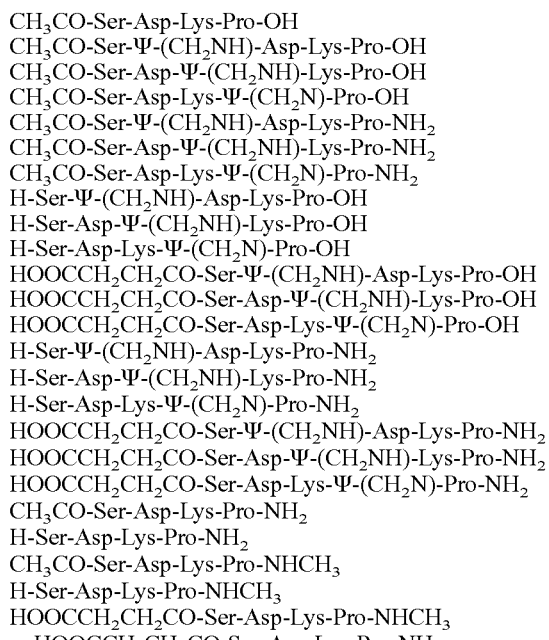

CH₃CO-Ser-Asp-Lys-Pro-OH
CH₃CO-Ser-Ψ-(CH₂NH)-Asp-Lys-Pro-OH
CH₃CO-Ser-Asp-Ψ-(CH₂NH)-Lys-Pro-OH
CH₃CO-Ser-Asp-Lys-Ψ-(CH₂N)-Pro-OH
CH₃CO-Ser-Ψ-(CH₂NH)-Asp-Lys-Pro-NH₂
CH₃CO-Ser-Asp-Ψ-(CH₂NH)-Lys-Pro-NH₂
CH₃CO-Ser-Asp-Lys-Ψ-(CH₂N)-Pro-NH₂
H-Ser-Ψ-(CH₂NH)-Asp-Lys-Pro-OH
H-Ser-Asp-Ψ-(CH₂NH)-Lys-Pro-OH
H-Ser-Asp-Lys-Ψ-(CH₂N)-Pro-OH
HOOCCH₂CH₂CO-Ser-Ψ-(CH₂NH)-Asp-Lys-Pro-OH
HOOCCH₂CH₂CO-Ser-Asp-Ψ-(CH₂NH)-Lys-Pro-OH
HOOCCH₂CH₂CO-Ser-Asp-Lys-Ψ-(CH₂N)-Pro-OH
H-Ser-Ψ-(CH₂NH)-Asp-Lys-Pro-NH₂
H-Ser-Asp-Ψ-(CH₂NH)-Lys-Pro-NH₂
H-Ser-Asp-Lys-Ψ-(CH₂N)-Pro-NH₂
HOOCCH₂CH₂CO-Ser-Ψ-(CH₂NH)-Asp-Lys-Pro-NH₂
HOOCCH₂CH₂CO-Ser-Asp-Ψ-(CH₂NH)-Lys-Pro-NH₂
HOOCCH₂CH₂CO-Ser-Asp-Lys-Ψ-(CH₂N)-Pro-NH₂
CH₃CO-Ser-Asp-Lys-Pro-NH₂
H-Ser-Asp-Lys-Pro-NH₂
CH₃CO-Ser-Asp-Lys-Pro-NHCH₃
H-Ser-Asp-Lys-Pro-NHCH₃
HOOCCH₂CH₂CO-Ser-Asp-Lys-Pro-NHCH₃
HOOCCH₂CH₂CO-Ser-Asp-Lys-Pro-NH₂.

9. The method according to claim 6, wherein the compound of formula (I) is represented by the formula: CH₃CO-Ser-Asp-Lys-Pro-OH.

10. The method according to claim 6, wherein the compound of formula (I) is present in the composition in an amount ranging from 0.01% to 10% by weight with respect to the total weight of the composition.

\* \* \* \* \*

UNITED STATES PATENT AND TRADEMARK OFFICE
CERTIFICATE OF CORRECTION

PATENT NO. : 8,697,652 B2
APPLICATION NO. : 11/630264
DATED : April 15, 2014
INVENTOR(S) : Bakala et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1940 days.

Signed and Sealed this
Twenty-ninth Day of September, 2015

Michelle K. Lee
*Director of the United States Patent and Trademark Office*